United States Patent [19]

Holtermann

[11] Patent Number: 5,082,988
[45] Date of Patent: Jan. 21, 1992

[54] ISOMERIZATION CATALYST AND PROCESS FOR ITS USE

[75] Inventor: Dennis L. Holtermann, Crockett, Calif.

[73] Assignee: Chevron Corporation, San Francisco, Calif.

[21] Appl. No.: 376,972

[22] Filed: Jul. 6, 1989

Related U.S. Application Data

[63] Continuation of Ser. No. 150,182, Jan. 29, 1988, abandoned.

[51] Int. Cl.$^5$ .................................................. C07C 5/13
[52] U.S. Cl. ...................................... 585/739; 585/751
[58] Field of Search ............................... 585/739, 751

[56] References Cited

U.S. PATENT DOCUMENTS

| | | | |
|---|---|---|---|
| 3,308,069 | 3/1967 | Wadlinger et al. | 208/111 |
| 3,923,641 | 12/1975 | Morrison | 208/111 |
| 4,419,220 | 12/1983 | LaPierre et al. | 208/120 |
| 4,501,926 | 2/1985 | LaPierre et al. | 585/739 |
| 4,518,485 | 5/1985 | LaPierre et al. | 585/739 |
| 4,554,065 | 11/1985 | Albinson et al. | 585/739 |
| 4,554,145 | 11/1985 | Rubin | 502/62 |
| 4,642,226 | 2/1987 | Calvert et al. | 502/202 |

FOREIGN PATENT DOCUMENTS 1210335 10/1979 United Kingdom.

Primary Examiner—Asok Pal
Assistant Examiner—E. D. Irzinski
Attorney, Agent, or Firm—Burns, Doane, Swecker & Mathis

[57] ABSTRACT

The present invention is a process and a catalyst for isomerizing normal and slightly branched $C_4$ to $C_7$ hydrocarbons. The catalyst comprises a Group VIII metal on Beta zeolite.

7 Claims, 2 Drawing Sheets

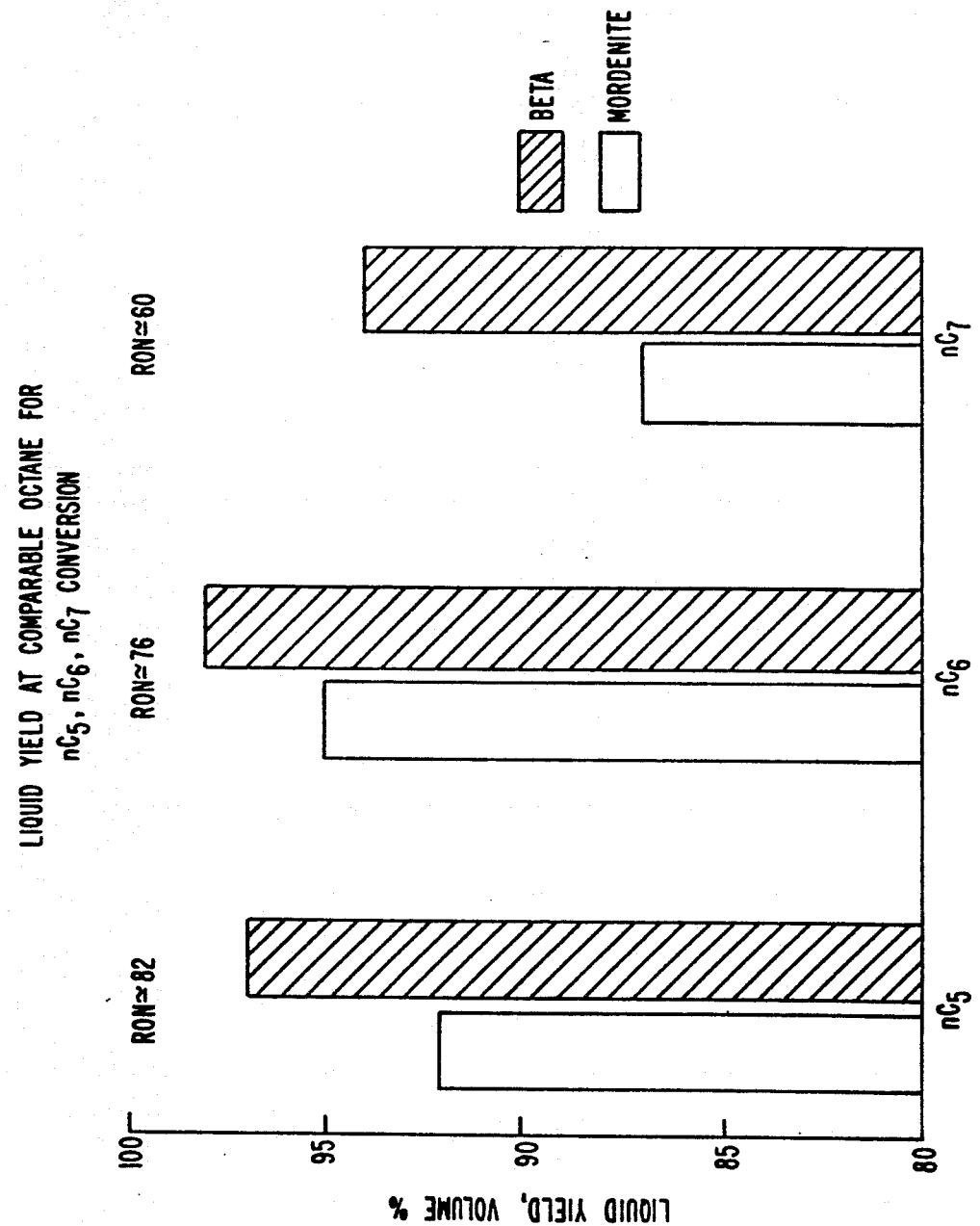

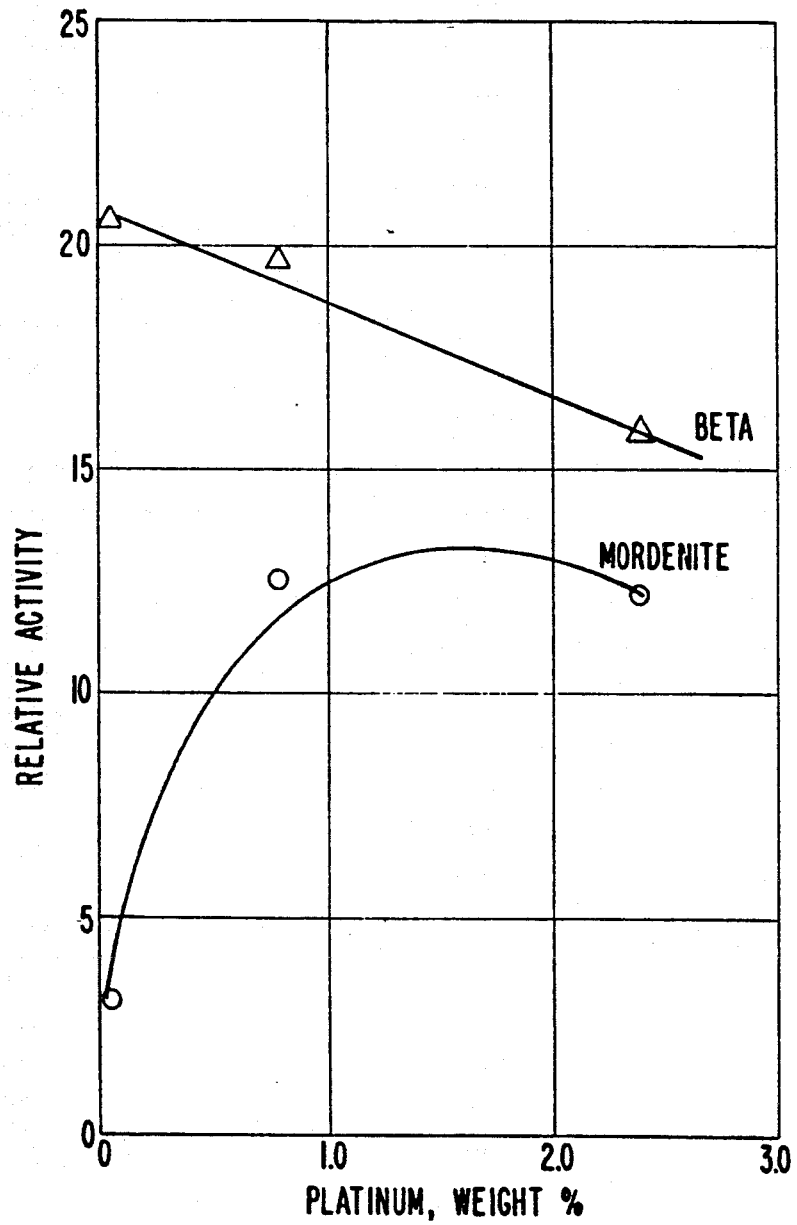
FIG._2.

ISOMERIZATION CATALYST AND PROCESS FOR ITS USE

This application is a continuation of application Ser. No. 07/150,182, filed Jan. 29, 1988, now abandoned.

FIELD OF THE INVENTION

The present invention is a process for alkane isomerization. More specifically, the present invention is a process for isomerizing $C_4$ to $C_7$ paraffins to increase their octane rating.

BACKGROUND OF THE INVENTION

The petroleum distillate fraction that contains $C_4$ to $C_7$ hydrocarbons is relatively low in octane because it contains substantial amounts of low octane, normal paraffins. For example, normal $C_5$ has a blending RON of 62 and normal $C_6$ has a blending RON of 19 (blending RON will be hereinafter called "RON"). However, when these paraffins are isomerized to form branched paraffins, their RON increases dramatically. For example, isopentane (2-methylbutane) has a RON of 99 and isohexane (2-methylpentane) has a RON of 83. Generally, the RON will increase with even higher branching (e.g., 2,2-dimethylbutane has a RON of 89).

Several catalysts have been used to isomerize these lower octane paraffins into the branched, higher octane paraffins. Examples are shown in U.S. Pat. No. 4,374,296 issue Feb. 15, 1983 to Haag et al.; U.S. Pat. No. 3,432,568 issued Mar. 11, 1969 to Miale et al.; U.S. Pat. No. 3,673,267 issued June 27, 1972 to Chen et al.; and U.S. Pat. No. 4,665,272 issued May 12, 1987 to Bakas et al. Haag et al. disclose isomerizing paraffins using intermediate pore zeolites, which have a constraint index between 1 and 12. Miale et al. describe hydroisomerizing saturated aliphatic and cyclic hydrocarbons by contacting them with a dual functional catalyst comprising mordenite and a catalytic metal. Chen et al. describe a process for isomerizing paraffins using mordenite having a silica to alumina ratio between 20:1 and 60:1. Bakas et al. disclose isomerizing paraffins using a crystalline aluminosilicate having a catalytic metal.

However, even though these prior art catalysts are useful, there remains a need for a new catalyst that is: (1) highly active; (2) highly selective for producing high octane liquid product; and (3) sulfur tolerant. That need is satisfied by the invention that is detailed below.

SUMMARY OF THE INVENTION

According to the present invention, a catalyst and a process for using the catalyst are provided for isomerizing $C_4$ to $C_7$ hydrocarbons. The catalyst comprises a Group VIII metal and Beta zeolite and the process comprises contacting the catalyst with a feed having normal and branched $C_4$ to $C_7$ hydrocarbons under isomerization conditions. Preferably, the Group VIII metal is platinum and the feed substantially comprises normal and singly branched lower octane $C_5$ and $C_6$ hydrocarbons. To improve catalytic activity the catalyst is preferably calcined in a steam/air mixture at an elevated temperature after impregnation with the Group VIII metal.

Among other factors, the present invention is based on my finding that a catalyst comprising Beta zeolite and a Group VIII metal is highly active and highly selective for isomerizing $C_5$ and $C_6$ hydrocarbons. The catalyst is also surprisingly selective for isomerizing $C_7$ hydrocarbons. Additionally, the catalyst is relatively sulfur tolerant. Furthermore, when the catalyst is calcined in a steam/air mixture, higher activity and selectivity are achieved.

More specifically, the process for alkane isomerization comprises contacting a feed containing low octane normal and singly branched $C_5$ and $C_6$ hydrocarbons and less than 0.1 ppm sulfur with a catalyst which comprises Beta zeolite and between 0.1% and 1.0% platinum, at a temperature between 400° F. and 600° F., at a pressure between 100 and 500 psig, a $H_2/HC$ ratio between 1 and 8, and between 1 and 4 LHSV.

BRIEF DESCRIPTION OF THE DRAWINGS

FIG. 1 is a comparative graph showing the relative conversion liquid yields in Volume %, of normal $C_5$, $C_6$ and $C_7$, respectively and the RON (Research Octane Number) of the isomerate produced using Beta zeolite and mordenite containing the same amount of platinum, as given in Example 1 through 3.

FIG. 2 is a graph of relative activity of Beta zeolite and mordenite catalyst with varying amounts of platinum impregnated therein.

DETAILED DESCRIPTION OF THE INVENTION

The following discussion presents a more detailed discussion of the present catalyst.

The Catalyst

Beta zeolite is a large pore zeolite. Large pore zeolites typically have effective pore diameters between 6 and 8 Angstroms (Å). Beta zeolite has a pore opening of approximately 7 Å. Although its present structure is unknown, it is believed to have pore windows formed by twelve-membered rings of silicon and aluminum atoms.

Beta zeolite is substantially shown and described in U.S. Pat. No. 3,308,069 and Re 28,341 to Wadlinger et al., and Breck, "Zeolite Molecular Sieves", p. 309 (1984), which are all hereby incorporated by reference in their entireties. These references describe a process for making Beta zeolite, its elemental composition and formula.

Preferably, the Beta zeolite of the present invention has a silica to alumina molar ratio between 10 and 1000, more preferably between 15 and 100. It is also preferable that the catalyst have high acidity. The catalyst's acidity can be increased by ammonium ion exchange and subsequent calcination to yield the hydrogen form. In addition to the hydrogen form, other forms of the zeolite can be used if they are sufficiently acidic. Preferably, the catalyst is substantially free of alkali or alkaline earth metals.

Preferably, catalysts of the present invention contain one or more Group VIII metals, e.g., nickel, ruthenium, rhodium, palladium, iridium or platinum. The preferred Group VIII metals are iridium, palladium, and most preferably platinum. The preferred percentage of the Group VIII metal in the catalyst is between 0.05% and 5%, more preferably between 0.1% and 2.5%, most preferably between 0.1% and 1.0%.

Group VIII metals are preferably introduced into Beta zeolite by impregnation, occlusion, or exchange in an aqueous solution of an appropriate salt. When it is desired to introduce two Group VIII metals into Beta zeolite, the operation may be carried out simultaneously or sequentially. Preferably, the Group VIII metal is highly dispersed within, and on, the zeolite.

By way of example, platinum can be introduced by impregnation with an aqueous solution of tetraammineplatinum (II) nitrate, tetraammineplatinum (II) hydroxide, dinitrodiamino-platinum or tetraammineplatinum (II) chloride. In an ion exchange process, platinum can be introduced by using cationic platinum complexes such as tetraammineplatinum (II) nitrate. On the other hand, when platinum is introduced into the zeolite by occlusion a platinum complex is preferably introduced into the zeolite during its synthesis.

After the desired metal or metals have been introduced, the catalyst is preferably calcined in air, or air diluted with an inert gas. More preferably, the catalyst is calcined in a steam/air mixture at an elevated temperature after platinum impregnation.

Promoter metals can be added to the catalyst in the manner described above. These metals are preferably selected from Groups VIII, IVA, IB or VIB.

The zeolite is preferably bound with a porous matrix. The term "porous matrix" includes inorganic compositions with which the zeolite will effectively bond after appropriate thermal treatment. The matrix porosity can either be inherent or it can be introduced by chemical means. Satisfactory matrices include pumie, firebrick, diatomaceous earth and inorganic oxides. Preferred inorganic oxides include alumina, silica, naturally occuring or synthetic clays (for example, bentonite, kaolin, sepiolite, attapulgite, and halloysite). Silica or alumina are especially preferred.

Compositing the zeolite with an inorganic oxide matrix can be achieved by any suitable known method wherein the zeolite is intimately admixed with the oxide while the latter is in a hydrous state (for example, as a hydrous salt, hydrogel, wet gelatinous precipitate, or in a dried state, or combinations thereof). A convenient method is to prepare a hydrous mono or plural oxide gel or cogel using an aqueous solution of a salt or mixture of salts (for example, sodium silicate). Ammonium hydroxide (or a similar base) is added to the solution in an amount sufficient to precipitate the oxides in hydrous form. Then, the precipitate is washed to remove most of the water soluble salts and it is thoroughly admixed with the zeolite which is in a finely divided state. Water or lubricating agents can be added in an amount sufficient to facilitate shaping of the mix (e.g., by extrusion).

The Process

Once the catalyst has been formed it can be employed in any of the conventional types of process equipment known to the art. It may be employed in the form of pills, pellets, granules, broken fragments, or various special shapes. It can be disposed as a fixed or moving bed within a reaction zone, and the charging stock can be passed therethrough as a liquid, vapor, or mixed phase, and in upward, downward, or radial flow. Alternatively, it could be prepared for use in fluidized-solid processes, in which the charging stock is passed upward through a turbulent bed of finely divided catalyst. However, in view of the danger of attrition losses of the valuable catalyst and the well-known advantages of plug flow reactors either a fixed bed system or a dense-phase moving bed system is preferred. In a fixed bed system, the feed is preheated (by any suitable heating means) to the desired reaction temperature and then passed into a isomerization zone containing the catalyst. This isomerization zone may be one or more separate reactors with suitable means to maintain the desired temperature at the entrance to each reactor. After reaction, the products from any of the foregoing process variants are separated from the catalyst, reduced to atmospheric pressure, and fractionated to recover the various components thereof. Additionally, the process can be operated in once-through or, preferably, with recycle of normal paraffins. Recycle operations are within the knowledge of skilled practitioners.

As discussed above, the petroleum distillate fraction preferably contains normal and singly branched $C_4$ to $C_7$ Paraffins. The feed preferably contains few multiply branched components such as 2,2-dimethylbutane and 2,3-dimethylbutane. However, when the low octane paraffins are isomerized to form multiply branched paraffins (such as the dimethylbutanes, for example), the octane number increases dramatically. This is the function of the present catalyst.

The present catalyst is highly active and highly selective for isomerizing $C_4$ to $C_7$ hydrocarbons. This high selectivity means that in comparison to prior art catalysts, such as mordenite, a higher product yield can be achieved when the two catalysts are run to a given octane. It also means that a higher octane can be achieved when the two catalysts are run to produce a given liquid yield.

The present process comprises contacting the isomerization catalyst with a hydrocarbon feed under isomerization conditions. The feed is preferably a light straight run fraction, boiling within the range of 30° F. to 250° F. and preferably from 60° F. to 200° F. Preferably, the hydrocarbon feed for the process comprises a substantial amount of $C_4$ to $C_7$ normal and singly branched hydrocarbons, more preferably low octane $C_5$ and $C_6$ hydrocarbons.

The present in the process is preferably between 50 psig and 1000 psig, more preferably between 100 and 500 psig. The liquid hourly space velocity (LHSV) is preferably between about 1 to about 10 with a value in the range of about 1 to about 4 being more preferred. It is also preferable to carry out the isomerization reaction in the presence of hydrogen. Preferably, hydrogen is added to give a hydrogen to hydrocarbon ratio ($H_2$/HC) of between 0.5 and 10, more preferably between 1 and 8. The temperature is preferably between about 200° F. and about 1000° F., more preferably between 400° F. and 600° F. As is well known to those skilled in the isomerization art, the initial selection of the temperature within this broad range is made primarily as a function of the desired conversion level considering the characteristics of the feed and of the catalyst. Thereafter, to provide a relatively constant value for conversion, the temperature may have to be slowly increased during the run to compensate for any deactivation that occurs.

The present catalyst is relatively sulfur tolerant. Nonetheless, a low sulfur feed is especially preferred in the present process. The feed preferably contains less than 10 ppm, more preferably less than 1 ppm, and most preferably less than 0.1 ppm sulfur. In the case of a feed which is not already low in sulfur, acceptable levels can be reached by hydrotreating the feed in a pretreatment zone with a hydrotreating catalyst which is resistant to sulfur poisoning. Sulfur can be subsequently removed as hydrogen sulfide in the gas phase after condensation of the liquid product. An example of a suitable catalyst for this hydrodesulfurization process is an alumina-containing support and a minor catalytic proportion of molybdenum oxide, cobalt oxide and/or nickel oxide. Hydrodesulfurization is typically conducted at 315° C. to 455° C., at 200 to 2000 psig, and at a liquid hourly space velocity of 1 to 5.

It is also preferable to limit the nitrogen level and the water content of the feed. Catalysts and processes which are suitable for these purposes are known to those skilled in the art.

After a period of operation the catalyst can become deactivated by sulfur or coke. Sulfur and coke can be removed from the catalyst using procedures that are known to those skilled in the art.

The present invention will be more fully understood by reference to the following examples. They are intended to be purely exemplary and are not intended to limit the scope of the invention in any way.

EXAMPLES

Example 1

In a 2-liter glass liner, 8.29 gms of Mallinkrodt sodium aluminate ($Na_2O.Al_2O_3.3H_2O$) was dissolved in 259.6 gms of an aqueous solution containing 20% tetraethyl ammonium hydroxide (Aldrich). 207.5 Grams of Ludox AS-30 colloidal silica was added in a thin stream while the solution was vigorously stirred. The liner was placed in a 2-liter Parr stainless steel bomb and statically heated for 6 days at 150° C. The solid, precipitate product was washed and dried, after which it was determined to be Beta zeolite by X-ray diffraction.

Beta zeolite was made more catalytically active by converting it into its hydrogen (proton) form as follows. Beta zeolite was layered in a thin bed and incrementally heated to 1000° F. at a rate of 150°/hr. The temperature was maintained at 1000° F. for 5 hours and then it was increased to 1100° F. for 4 more. The calcined zeolite was ion-exchanged by 4 successive treatments with $NH_4NO_3$. Each treatment used the same mass of $NH_4NO_3$ to zeolite (a slurry of about 50 gr. zeolite/liter $H_2O$) and the solution was refluxed for at least 2 hours. The sodium content of the zeolite was low after the fourth exchange. The zeolite was filtered, washed, dried and recalcined as above while omitting the 1100° F. heating step.

The final Beta zeolite as impregnated with enough tetraamine platinum nitrate to achieve 0.8 wt.% platinum. Thereafter, the impregnated catalyst was dried at 250° F. for approximately 14 hours then calcined at 500° F. for 3 hours, and then reduced.

Example 2

The catalyst of Example 1 was used to isomerize a feed which substantially comprised normal and branched $C_5$ and $C_6$ hydrocarbons. The isomerization conditions where 1 LHSV, 200 psig, 6 $H_2$/HC, and 520° F. The feed composition and the isomerization results are shown in Table I.

TABLE I

| Compound (Wt. %) | Feed | Isomerate |
|---|---|---|
| Methane | 0.00 | 0.00 |
| Ethane | 0.00 | 0.00 |
| Propane | 0.00 | 0.71 |
| Isobutane | 0.04 | 1.84 |
| N-butane | 0.28 | 0.64 |
| Iso-$C_5$ | 12.03 | 21.45 |
| N-pentane | 18.93 | 11.37 |
| 2,2-DMB | 0.58 | 9.56 |
| Cyclo-$C_5$ | 4.26 | 3.69 |
| 2,3-DMB | 2.26 | 4.44 |

TABLE I-continued

| Compound (Wt. %) | Feed | Isomerate |
|---|---|---|
| 2MP | 12.55 | 15.36 |
| 3MP | 8.19 | 10.11 |
| N-hexane | 19.74 | 8.46 |
| MCP | 15.04 | 9.82 |
| Benzene | 3.75 | 0.00 |
| CHX | 1.89 | 2.56 |
| $C_7$+ | 0.45 | 0.00 |
| $C_5$ + Wt. % | 99.68 | 96.81 |
| LV % | 100.00 | 99.01 |
| RON | 74.50 | 80.08 |

Example 3

A commercial mordenite (Zeolon 100 H) was obtained from Norton Chemical Company and platinum impregnated as in Example 1. The final catalyst contained 0.8 wt.% platinum.

Example 4

This example compares the liquid yields achievable with the catalysts of Example 1 and Example 3, which both contained 0.8% platinum.

Both catalysts were used to isomerize normal $C_5$, $C_6$, $C_7$ pure component feeds at 500° F., 100 psig, and 6$H_2$/HC. The liquid yields and corresponding octanes that were obtained for the two catalysts are shown in FIG. 1.

Example 5

Platinum was impregnated onto samples of Beta zeolite and mordenite at varying levels. Both catalysts were used to isomerize a normal hexane feed at 510° F., 100 psig, 3 LHSV, and 6$H_2$HC. The results are shown in Table II. The relative intrinsic activity for each catalyst at low conversion was calculated and is shown in FIG. 2.

TABLE II

| Catalyst Support | Pt | n$C_6$ Conv. | LV % | Isomerate RON |
|---|---|---|---|---|
| H-Beta | 2.4 | 84 | 94 | 76.0 |
|  | 0.8 | 83 | 97 | 76.1 |
|  | 0.05 | 82 | 98 | 75.3 |
| H-Mordenite | 2.4 | 80 | 92 | 74.1 |
|  | 0.8 | 82 | 95 | 75.1 |
|  | 0.05* | 76 | 90 | 64.5 |

*Temp. raised to 540° F. due to low activity.

Example 6

This example demonstrates the effect of sulfur on platinum/Beta zeolite and platinum/mordenite catalysts. Each catalyst was contacted with the feed of Table I at 520° F., 200 psig, 6$H_2$HC, and 1 LHSV for 24 hours. Then $H_2S$ was continuously added to the reactor inlet $H_2$ and into the feed for 24 hours. The $H_2S$ addition rate was sufficient to give approximately 250 ppm sulfur on a feed weight basis. Thereafter, the $H_2S$ was removed and the catalysts were only contacted with clean feed and clean hydrogen. The results are shown in Table III.

TABLE III

| Catalyst | Time | ppm Sulfur (Feed Wt. Basis) | Yield (LV %) | RON (Calc.) |
|---|---|---|---|---|
| 0.3% Pt on | 0–24 | 0 | 95.3 | 79.9 |
| Mordenite | 24–48 | 234 | 86.5 | 80.2 |
|  | 48–72 | 0 | 95.2 | 79.7 |

TABLE III-continued

| Catalyst | Time | ppm Sulfur (Feed Wt. Basis) | Yield (LV %) | RON (Calc.) |
|---|---|---|---|---|
| 0.3% Pt on | 0–24 | 0 | 97.5 | 79.7 |
| Beta Zeolite | 24–48 | 234 | 95.3 | 79.7 |
| | 48–72 | 0 | 97.3 | 79.2 |

The conventional platinum on mordenite catalyst suffers a relatively larger loss in liquid yield than platinum on Beta zeolite catalyst. Additionally, when sulfur is withdrawn, both catalysts recover from sulfur poisoning, but the liquid yield from the platinum/Beta zeolite is relatively higher.

Example 7

This example demonstrates a preferred method of platinum loading which includes a steam calcination step after platinum impregnation.

Beta zeolite was prepared in the manner set forth in Example 1. Platinum was impregnated onto the Beta zeolite to achieve 0.3 wt.% and then samples of the catalyst were subjected to different calcination treatments. The different catalysts were then used to isomerize the feed of Table I at 200 psig, 1 LHSV, 6 $H_2$/HC, for 20 hours. The results are shown in Table IV.

TABLE IV

| Catalyst | Calcination Conditions | Reaction Temperature | Isomerate Properties | | | |
|---|---|---|---|---|---|---|
| | | | i/nC$_5$ | 2,2-DMB/nC$_6$ | Yield (LV %) | RON (Calc.) |
| 0.3% Pt/ Beta | 500° F. in Air | 520° F. | 1.7 | 0.6 | 97.4 | 79.5 |
| 0.3% Pt/ Beta | 500° F. in 50% Steam/ 50% Air | 515° F. | 1.8 | 1.0 | 97.8 | 79.9 |
| 0.3% Pt/ Beta | 600° F. in 50% Steam/ 50% Air | 520° F. | 2.1 | 0.9 | 97.0 | 80.1 |

When the catalysts were calcined in a steam/air mixture, the product ratios of iso to normal C$_5$ hydrocarbons (i/nC$_5$) and 2,2-dimethylbutane to normal C$_6$-hydrocarbons (2,2-DMB/nC$_6$) increased, which in turn increased the product RON. Additionally, this increase was achieved at a lower reaction temperature which indicated an increase in catalyst activity.

The embodiments of this invention which are exemplified above are intended solely as illustrations of the invention. They should not be interpreted as limiting the scope of the invention to just those features which are shown or disclosed. As those familiar with this area of research will appreciate, there are numerous variations of the invention as defined in the following claims which may have not been exemplified but which will achieve equivalent results.

What is claimed is:

1. A process for isomerizing a feedstream of predominantly normal and singly branched C$_5$ to C$_7$ hydrocarbons to form an isomerate having a greater concentration of doubly and singly branched hydrocarbons and a substantially higher RON than said feedstream comprising contacting a catalyst formed of an acidic beta zeolite having between 0.05 and 5 wt% of at least one Group VIII metal, with a feedstream having predominantly normal or singly branched C$_5$ to C$_7$ components at a temperature from about 400° F. to about 600° F., at a pressure between about 50 psig and about 1000 psig, an $H_2$/HC ratio between about 0.5 and 10 and an LHSV of between about 1 and 10 to form an isomerate having a substantial increase in both the multiply and singly branched paraffins and having an RON greater than said feedstream.

2. A process in accordance with claim 1 wherein after formation of said catalyst, including said beta Zeolite and said at least one Group VIII metal, the catalyst is calcined in a steam and air mixture at an elevated temperature.

3. A process in accordance with claim 1 wherein said at least one Group VIII metal includes platinum.

4. A process in accordance with claim 3 wherein said platinum is between about 0.1% wt% and about 2.5 wt % of the catalyst.

5. A process for alkane isomerization to increase substantially the octane rating of a feedstream of predominantly normal or singly branched C$_5$ to C$_7$ hydrocarbon components while maintaining a high liquid volume conversion which comprises contacting a catalyst comprising an acidic Beta zeolite and between 0.1 wt % and 2.5 wt % platinum, with said feedstream having a sulfur content of from about 0.1 ppm to about 250 ppm at a temperature of from about 400° F. to about 600° F. at a pressure between about 100 psig and 500 psig, a $H_2$/HC ratio between about 1 and about 8, and between about 1 and about 4 LHSV to yield an isomerate of multiply and singly branched alkanes and an octane number substantially greater than said feedstream and without substantial decrease in the liquid volume % of said isomerate.

6. A process in accordance with claim 5 wherein said platinum is impregnated in said Beta zeolite and after formation of said catalyst said catalyst is calcined in a steam and air mixture at an elevated temperature and said contacting of said catalyst with said feedstream is at a temperature below about 550° F. to increase further the yield of said multiply branched alkanes.

7. A process in accordance with claim 5 wherein said feedstream has a sulfur content of less than about 0.1 ppm.

* * * * *